US012714332B2

(12) United States Patent
Carrera et al.

(10) Patent No.: US 12,714,332 B2
(45) Date of Patent: Aug. 25, 2026

(54) AUTOMATIC SEGMENTATION OF INERTIAL SENSOR DATA

(71) Applicants: STMicroelectronics International N.V., Geneva (CH); POLITECNICO DI MILANO, Milan (IT)

(72) Inventors: Diego Carrera, Lodi (IT); Carlo Ghiglione, Genoa (IT); Beatrice Rossi, Milan (IT); Pasqualina Fragneto, Burago di Molgora (IT); Giacomo Boracchi, Buccinasco (IT)

(73) Assignees: STMicroelectronics International N.V ., Geneva (CH); Politecnico di Milano, Milan (IT)

( * ) Notice: Subject to any disclaimer, the term of this patent is extended or adjusted under 35 U.S.C. 154(b) by 526 days.

(21) Appl. No.: 18/458,879

(22) Filed: Aug. 30, 2023

(65) Prior Publication Data

US 2025/0072787 A1 Mar. 6, 2025

(51) Int. Cl.
*A61B 5/11* (2006.01)
*A61B 5/00* (2006.01)

(52) U.S. Cl.
CPC ........... *A61B 5/1118* (2013.01); *A61B 5/1126* (2013.01); *A61B 5/726* (2013.01)

(58) Field of Classification Search
CPC ..... A61B 5/1118; A61B 5/1126; A61B 5/726; A61B 5/7264; A61B 5/1123
See application file for complete search history.

(56) References Cited

U.S. PATENT DOCUMENTS

| | | | | |
|---|---|---|---|---|
| 2,605,340 A * | 7/1952 | Disney | G08C 15/04 | 340/870.18 |
| 3,657,918 A * | 4/1972 | Hurlbert | G01C 19/44 | 74/5.6 R |
| 3,788,579 A * | 1/1974 | Sliney | G05D 1/0202 | 244/184 |
| 4,106,094 A * | 8/1978 | Land | G01C 21/165 | 244/175 |

(Continued)

FOREIGN PATENT DOCUMENTS

| | | |
|---|---|---|
| CN | 113280832 A | 8/2021 |
| WO | WO 2022063828 A1 | 3/2022 |

OTHER PUBLICATIONS

Böttcher et al., "Detecting Transitions in Manual Tasks from Wearables: An Unsupervised Labeling Approach," *Informatics* 5:16, 2018. (18 pages).

(Continued)

*Primary Examiner* — Bhavesh V Amin
(74) *Attorney, Agent, or Firm* — Seed Intellectual Property Law Group LLP

(57) ABSTRACT

A method of operating an inertial sensor module includes receiving a stream of inertial sensor data representing activity of a user of an electronic device and generating a plurality of wavelet sub-bands by performing a wavelet transform on the inertial sensor data. The method includes identifying a wavelet sub-band of highest energy from the plurality of wavelet sub-bands, generating augmented inertial sensor data by combining the wavelet sub-band of highest energy to the inertial sensor data, and identifying a first transition in the activity of the user based on the augmented inertial sensor data.

20 Claims, 11 Drawing Sheets

(56) References Cited

U.S. PATENT DOCUMENTS 4,254,465 A * 3/1981 Land .................... G01C 21/185 244/175
4,303,978 A * 12/1981 Shaw ................... G01C 21/183 701/506
4,608,641 A * 8/1986 Snell .................... G01C 21/185 701/4
5,008,825 A * 4/1991 Nadkarni ............. G05D 1/0083 701/4
5,166,882 A * 11/1992 Stambaugh ............. G01P 21/00 33/324
5,194,872 A * 3/1993 Musoff ................ G01C 21/188 73/1.77
5,410,487 A * 4/1995 Okayama ............. G01C 21/188 73/178 R
5,527,003 A * 6/1996 Diesel .................... G05D 1/101 244/76 R
5,598,166 A * 1/1997 Ishikawa ................. G01S 19/49 342/357.3
5,646,857 A * 7/1997 McBurney ............... G01C 5/00 701/489
5,784,029 A * 7/1998 Geier ...................... G01S 19/49 701/472
6,175,807 B1 * 1/2001 Buchler ............... G01C 21/183 701/534
6,269,306 B1 * 7/2001 Ibrahim ............... G01C 21/165 701/472
6,374,190 B2 * 4/2002 Schupfner ............. G01C 25/00 702/94
6,577,952 B2 * 6/2003 Geier ...................... G01S 19/49 701/472
6,622,091 B2 * 9/2003 Perlmutter ........... G01C 25/005 701/472
6,738,721 B1 * 5/2004 Drucke ................ G01C 21/188 73/1.37
6,782,315 B2 * 8/2004 Lu ........................... B62D 6/04 280/735
6,859,727 B2 * 2/2005 Bye ...................... G01C 21/188 701/536
6,904,377 B2 * 6/2005 Liu ...................... G01C 21/188 702/41
7,103,477 B1 * 9/2006 Lee ...................... G01C 21/183 73/488
7,130,744 B2 * 10/2006 Krings ................. G01C 21/188 701/472
7,185,858 B2 * 3/2007 Wang ................... G01C 25/005 244/171
7,196,317 B1 * 3/2007 Meissner, II .......... G01J 1/4228 385/13
7,328,104 B2 * 2/2008 Overstreet .............. G01S 19/47 701/472
7,471,451 B2 * 12/2008 Dent ...................... G02B 15/04 359/421
7,561,784 B2 * 7/2009 Wescott ................. G01C 21/18 396/13
7,606,665 B2 * 10/2009 Weed ................... G01C 25/005 701/503
7,671,311 B2 * 3/2010 Ellison ................... F16M 11/10 74/5.34
7,920,981 B2 * 4/2011 Fennel ................. G01D 18/008 701/33.1
7,965,223 B1 * 6/2011 McCusker ............... G08G 5/54 340/963
8,331,888 B2 * 12/2012 Halladay ................. G01S 19/03 334/7
8,558,150 B2 * 10/2013 Chappell .................. H05B 1/02 73/488
8,577,633 B2 * 11/2013 Patel ...................... G01C 25/00 73/504.18
8,583,371 B1 * 11/2013 Goodzeit ........... G01C 19/5776 701/501
8,726,717 B2 * 5/2014 Supino ................. G01C 25/005 73/1.77
8,798,450 B2 * 8/2014 Aicher ................... G01C 21/18 396/13
9,008,988 B2 * 4/2015 Dusha .................. G01C 21/183 702/104
9,104,271 B1 * 8/2015 Adams .................. G06F 3/0233
9,151,613 B2 * 10/2015 Czompo ............. G01C 21/165
9,228,836 B2 * 1/2016 Girod ..................... G01C 15/00
9,250,083 B2 * 2/2016 Czompo ................. G01S 19/49
9,341,718 B2 * 5/2016 Vanderwerf ............ G01S 19/28
9,354,080 B2 * 5/2016 Buchanan .............. G01C 19/00
9,501,803 B2 * 11/2016 Bilac ...................... G06Q 50/06
9,517,055 B2 * 12/2016 Zalev .................. A61B 8/4416
9,652,955 B1 * 5/2017 Ray ....................... H04W 4/023
9,683,849 B2 * 6/2017 Zhi ....................... G01C 21/18
9,712,738 B2 * 7/2017 Van Heugten ....... H04N 23/959
9,752,879 B2 * 9/2017 Al-Hamad ........... G01C 21/183
9,928,359 B1 * 3/2018 Vargas ................... G06F 21/78
10,015,618 B1 * 7/2018 Kleijn ..................... H04S 7/303
10,101,174 B2 * 10/2018 Ell ....................... G01C 21/185
10,132,635 B2 * 11/2018 Kazemipur ........ G01C 21/1656
10,180,499 B2 * 1/2019 Lee ....................... H04W 4/027
10,267,924 B2 * 4/2019 Ramanandan .......... G01S 19/52
10,271,766 B1 * 4/2019 Parker, Jr. ............ A61B 5/0833
10,335,060 B1 * 7/2019 Kahn ................... A61B 5/7246
10,532,266 B2 * 1/2020 Genova ................... H04W 4/21
10,539,421 B2 * 1/2020 Sheard ...................... F41G 7/36
10,539,644 B1 * 1/2020 Alarcon Herrera ....... G01S 1/70
10,849,134 B2 * 11/2020 Islam ................. H04W 72/542
10,859,713 B2 * 12/2020 Niesen .................... G01S 19/49
10,871,374 B2 * 12/2020 Petillon ................... G01S 19/49
11,150,090 B2 * 10/2021 Rizzardini ........... G01K 15/002
11,193,896 B2 * 12/2021 Stewart .................. G01B 21/20
11,199,410 B2 * 12/2021 Jain ...................... G01C 21/165
11,506,818 B1 * 11/2022 Chenard ........... G02B 6/02323
11,529,073 B1 * 12/2022 Parker, Jr. ............ A61B 5/0015
11,656,081 B2 * 5/2023 Paniccia ............. G01C 19/728 73/504.01
11,662,472 B2 * 5/2023 Bageshwar ........ G01C 21/1656 342/357.22
11,662,478 B2 * 5/2023 Reimer ................... G01S 19/44 342/352
11,703,522 B2 * 7/2023 Pan ........................ G01P 21/00 73/497
11,721,235 B2 * 8/2023 Skarica .................... G09B 9/22 434/48
11,747,142 B2 * 9/2023 Jain ........................ G01S 19/49 701/472
11,809,639 B2 * 11/2023 Morrison ............. G01C 21/165
11,860,287 B2 * 1/2024 Angelo ................. G01S 19/396
11,892,319 B2 * 2/2024 Ruppel .................. B60W 40/11
11,906,640 B2 * 2/2024 Reimer ................... G01S 19/41
11,940,277 B2 * 3/2024 Roumeliotis ............ G07C 5/08
11,959,748 B2 * 4/2024 Wu ...................... G01C 21/188
11,972,117 B2 * 4/2024 Meiri .................... G06F 3/0637
11,978,555 B2 * 5/2024 Sobol ...................... H04W 4/38
12,019,163 B2 * 6/2024 Mobarak ............... G01S 19/215
12,105,211 B2 * 10/2024 Carcanague ............ G01S 19/07
12,211,292 B2 * 1/2025 Buss .................... G06V 20/588
12,216,211 B2 * 2/2025 Cole ..................... G01S 19/071
12,297,927 B2 * 5/2025 Karatsinides ....... F16K 31/0658
12,366,666 B2 * 7/2025 Grgich ..................... G01S 19/20
12,375,366 B2 * 7/2025 Sobol .................... H04L 41/149
12,464,311 B2 * 11/2025 Mclachlan .............. H04L 67/52
12,482,211 B2 * 11/2025 Mclachlan .............. G06T 19/20
12,567,213 B2 * 3/2026 McLachlan ........... G06T 19/006
2007/0240486 A1 * 10/2007 Moore ................ G01C 21/183 73/504.03
2007/0287923 A1 * 12/2007 Adkins .............. A61B 5/02438 600/485
2008/0167814 A1 * 7/2008 Samarasekera .... G01C 21/1656 701/469
2009/0248304 A1 * 10/2009 Roumeliotis ...... G01C 21/1656 701/500
2011/0234397 A1 * 9/2011 Fetzer .................. G08B 25/016 340/539.13
2011/0245633 A1 * 10/2011 Goldberg ............... A61B 5/165 600/323

(56) References Cited

U.S. PATENT DOCUMENTS

2012/0221244 A1* 8/2012 Georgy .................. G01S 19/47 701/472
2012/0245839 A1* 9/2012 Syed .................... G01C 25/005 702/150
2013/0029681 A1* 1/2013 Grokop ................ G01C 22/006 455/456.1
2013/0054181 A1* 2/2013 Lakhzouri ............ G01C 22/006 702/141
2013/0158928 A1* 6/2013 Hogdal .................. G01C 21/06 73/1.38
2014/0142885 A1* 5/2014 Chowdhary ............ G06F 15/00 702/141
2014/0188638 A1* 7/2014 Jones ...................... H04W 8/22 705/16
2014/0297212 A1* 10/2014 Anderson ............ G01C 25/005 702/90
2014/0372026 A1* 12/2014 Georgy .................. G01S 19/47 701/469
2014/0375493 A1* 12/2014 Weisenburger ......... G01S 19/47 342/357.3
2015/0085179 A1* 3/2015 Van Heugten ....... H04N 23/673 348/349
2015/0143125 A1* 5/2015 Nix ...................... H04L 9/0861 713/171
2015/0164377 A1* 6/2015 Nathan ................ A61B 5/6802 600/595
2015/0244699 A1* 8/2015 Hessler ............... H04W 12/062 726/7
2015/0301338 A1* 10/2015 Van Heugten ..... G02B 27/0172 345/8
2015/0316579 A1* 11/2015 Pakzad ................ G01C 22/006 702/150
2015/0334554 A1* 11/2015 Song ..................... H04W 8/183 455/558
2015/0345952 A1* 12/2015 Chang .................... G01C 21/12 701/541
2015/0354951 A1* 12/2015 Ali ........................ G06F 3/0346 702/141
2016/0007158 A1* 1/2016 Venkatraman ........ H04W 4/023 455/456.2
2016/0018278 A1* 1/2016 Jeter, II .................. G16H 40/63 340/665
2016/0071383 A1* 3/2016 Baldwin ................. G06F 3/011 340/407.1
2016/0173359 A1* 6/2016 Brenner ............. A61B 5/02438 709/224
2016/0175091 A1* 6/2016 Van Heugten ............ A61F 2/14 623/6.22
2016/0294828 A1* 10/2016 Zakaria ............... H04L 63/0876
2016/0305782 A1* 10/2016 Al-Hamad ........... G01C 21/183
2016/0305784 A1* 10/2016 Roumeliotis ........... G06T 7/277
2016/0314255 A1* 10/2016 Cook .................... G06F 16/906
2017/0006003 A1* 1/2017 Zakaria ............... H04L 63/0442
2017/0017822 A1* 1/2017 Zimmerman ........ G06K 7/1452
2017/0031032 A1* 2/2017 Garin ...................... G01S 19/55
2017/0053267 A1* 2/2017 Abel .................. G06Q 20/4018
2017/0109656 A1* 4/2017 Cook ....................... G06N 5/02
2017/0134171 A1* 5/2017 Woxland ............. H04W 12/086
2017/0163685 A1* 6/2017 Schwartz ............ H04W 12/088
2017/0173262 A1* 6/2017 Veltz ...................... G16H 20/17
2017/0188895 A1* 7/2017 Nathan ................. A61B 5/1118
2017/0193787 A1* 7/2017 Devdas ................ G08B 25/005
2017/0202484 A1* 7/2017 Al-Shaery ................ A61B 5/08
2017/0208426 A1* 7/2017 Komoni .................. H04W 4/80
2017/0219716 A1* 8/2017 Niesen .................... G01S 19/47
2017/0219717 A1* 8/2017 Nallampatti Ekambaram ............ G01S 11/12
2017/0227656 A1* 8/2017 Niesen .................... G01S 19/47
2017/0237719 A1* 8/2017 Schwartz ............. G06F 21/602 713/153
2017/0272842 A1* 9/2017 Touma ............... A63B 24/0003
2018/0001184 A1* 1/2018 Tran ....................... G16H 50/20
2018/0042513 A1* 2/2018 Connor .................. A61B 5/369
2018/0085058 A1* 3/2018 Chakravarthi ......... G16H 40/67
2018/0168464 A1* 6/2018 Barnett, Jr. ........ A61B 5/02055
2018/0188384 A1* 7/2018 Ramanandan .......... G01S 19/47
2018/0247713 A1* 8/2018 Rothman ........... A61B 5/02055
2018/0375849 A1* 12/2018 Koskimies ............ H04L 9/3234
2019/0014048 A1* 1/2019 Krishna Singuru ......................... H04L 41/5041
2019/0057189 A1* 2/2019 Frederickson ....... G08B 21/043
2019/0147721 A1* 5/2019 Avitan .................. G06F 1/3209 340/573.1
2019/0208363 A1* 7/2019 Shapiro ................ A61B 5/0205
2020/0268261 A1* 8/2020 Ikegami .................. H04W 4/70
2020/0311347 A1* 10/2020 Theobald ................ G06F 40/35
2020/0367823 A1* 11/2020 Chahine ............... A61B 5/6807
2020/0400957 A1* 12/2020 Van Heugten ..... G02B 27/0172
2021/0169417 A1* 6/2021 Burton ................. A61B 5/4815
2021/0319894 A1* 10/2021 Sobol ..................... G16H 50/30
2021/0373676 A1* 12/2021 Jorasch ................. G06F 3/0383
2021/0374391 A1* 12/2021 Jorasch .................. G06V 40/19
2021/0399911 A1* 12/2021 Jorasch ............... H04L 12/1818
2021/0400142 A1* 12/2021 Jorasch ............... H04L 65/1069
2021/0405287 A1* 12/2021 Chenard ........... C03B 37/01274
2022/0006813 A1* 1/2022 Jorasch ................ A61B 5/6803
2023/0000410 A1* 1/2023 Woods .................... G06F 3/015
2023/0073174 A1* 3/2023 Clark ..................... G16H 20/30
2023/0253002 A1* 8/2023 Robben ................ H04R 1/1041 704/226
2023/0256191 A1* 8/2023 Woods .................. A61M 21/00 600/28
2023/0419981 A1* 12/2023 Robben ............... G10L 21/0324
2024/0021184 A1* 1/2024 Hussenbocus ....... G10K 11/178
2024/0274285 A1* 8/2024 Russek-Sobol .......... G06N 5/01
2026/0013728 A1* 1/2026 Ray ...................... A61B 5/0022
2026/0053442 A1* 2/2026 Burton ................. A61B 5/4815

OTHER PUBLICATIONS

Lima et al., "Human Activity Recognition Using Inertial Sensors in a Smartphone: An Overview," *Sensors 19*:3213, 2019. (28 pages).

Liu et al., "Change-Point Detection in Time-Series Data by Relative Density-Ratio Estimation," arXiv:1203.0453v2 [stat.ML], Jan. 16, 2013. (27 pages).

Romano et al., "Comparison between Chest-Worn Accelerometer and Gyroscope Performance for Heart Rate and Respiratory Rate Monitoring," *Biosensors 12*:834, 2022. (15 pages).

Truong et al., "Selective review of offline change point detection methods," arXiv:1801.00718v3 [cs.CE], Mar. 26, 2020. (58 pages).

* cited by examiner

110/112
110/112
110/112
t1
t2
t3
t4
t1
t2
t3
t4
t1
t2
t3
t4
t5
t6
t7
t8
t9

AUTOMATIC SEGMENTATION OF INERTIAL SENSOR DATA

BACKGROUND

Technical Field

The present disclosure generally relates to inertial sensors, and more particularly to analysis of inertial sensor data.

Description of the Related Art

Electronic devices often include inertial sensors. Inertial sensors have become an enabling technology in various applications and are currently present in many varieties of digital devices and intelligent vehicles/robots. Digital devices can use the inertial sensor information to facilitate localization, navigation, mapping, and to predict failures. Wearable inertial sensors are also frequently used in health care and sporting applications to capture movement patterns outside typical laboratory environments.

Machine learning methods for classification and regression of inertial data can be very useful to expand the possible applications of inertial sensors. For instance, machine learning methods can be used to classify human activities, detect diseases or risk status, or estimate continuous variables like walking speed. These can be used to learn the orientation of the sensor, vehicle motion, localization, mapping, or even monitor the health of robots, machines, and industrial equipment.

In many cases, training sets are utilized to train classifier models associated with inertial sensors. A training set could include a plurality of segments of inertial sensor data. Each segment corresponds to sensor data during a particular period of time. Each segment may represent a particular activity being performed by the user or machine, as the case may be. However, it can be very difficult to generate a training set that includes segments that only correspond to a single activity type and that do not include portions of multiple types. Even after a classifier model has been trained, it can be difficult for the classifier model to identify segments of sensor data that correspond only to a single activity.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

Embodiments of the present disclosure analyze inertial sensor data and effectively and efficiently divide the inertial sensor data into segments that each correspond to a single activity. Embodiments of the present disclosure perform wavelet transforms on a sliding window of inertial sensor data in order to generate augmented inertial sensor data. The sliding window is divided into a first half and a second half. A discrepancy value is calculated between the first half window and the second half window. Embodiments of the present disclosure identify transitions between activities based on the discrepancy value. In this way, embodiments of the present disclosure effectively and efficiently divide the inertial sensor data into segments that each correspond to a single activity. The segments can then be utilized in a training set for a machine learning process or for real time classification of activities.

In one embodiment, a method includes receiving a stream of inertial sensor data representing activity of a user of an electronic device, generating a plurality of wavelet sub-bands by performing a wavelet transform on the inertial sensor data, and identifying a wavelet sub-band of highest energy from the plurality of wavelet sub-bands. The method includes generating augmented inertial sensor data by combining the wavelet sub-band of highest energy to the inertial sensor data and identifying a first transition in the activity of the user based on the augmented inertial sensor data.

In one embodiment, a method includes receiving, from an inertial sensor, a stream of inertial sensor data corresponding to activity of a user of an electronic device that includes the inertial sensor, identifying a plurality of activity transitions in the inertial sensor data, and identifying a plurality of activity segments in the inertial sensor data, each activity segment corresponding to a portion of the sensor data between adjacent activity transitions. Identifying the activity transitions includes generating, for each of a plurality of subsets of the inertial sensor data, a plurality of wavelet sub-bands by performing a wavelet transform, selecting, for each subset, one of the wavelet sub-bands, and generating, for each subset of the inertial sensor data, an augmented data subset by combining the selected sub-band with the subset of the inertial sensor data.

In one embodiment, an electronic device, includes an inertial sensor configured to generate a stream of inertial sensor data based on activity of a user and a control circuit coupled to the inertial sensor. The control circuit is configured to receive the stream, generate a plurality of wavelet sub-bands by performing a wavelet transform on the inertial sensor data and identify a wavelet sub-band of highest energy from the plurality of wavelet sub-bands. The control circuit is configured to generate augmented inertial sensor data by combining the wavelet sub-band of highest energy to the inertial sensor data and identify a transition in the activity of the user based on the augmented inertial sensor data.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known systems, components, and circuitry associated with integrated circuits have not been shown or described in detail, to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to." Further, the terms "first," "second," and similar indicators of sequence are to be construed as interchangeable unless the context clearly dictates otherwise.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

Figure 1:
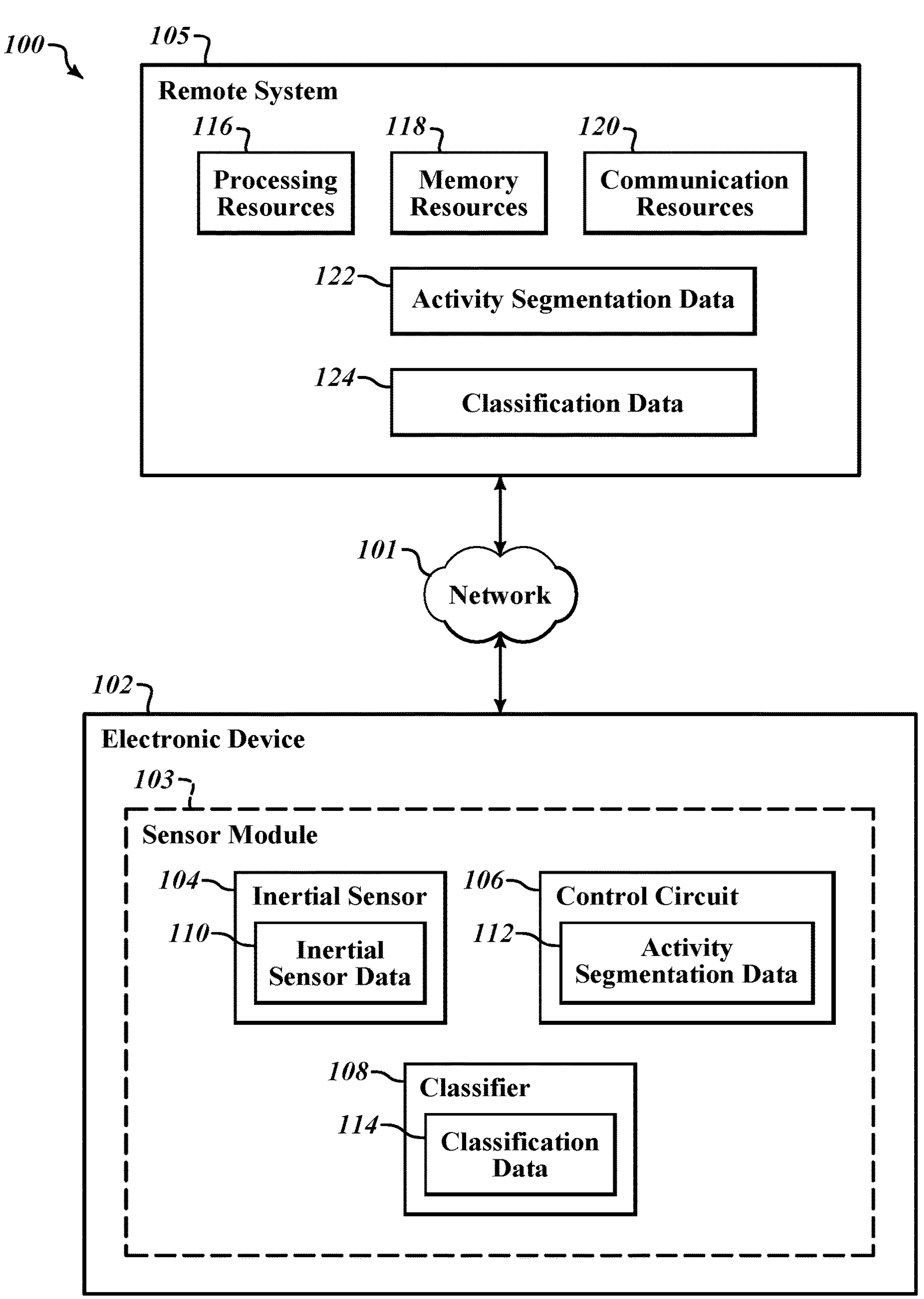
FIG. 1 is a block diagram of a system including an electronic device having an inertial sensor, in accordance with one embodiment.

FIG. 1 is a block diagram of a system 100, in accordance with one embodiment. The system 100 includes an electronic device 102 of the electronic device 102 includes a sensor module 103 having an inertial sensor 104. As will be set forth in more detail below, the components of the electronic device 102 cooperate to identify when inertial sensor data indicates a change from one activity to another activity. The result is that the inertial sensor data can be divided into segments that each represents a period of time during which the same activity is performed. This can assist in training a classifier to recognize activities and can also assist in classifying activities in real time.

The electronic device 102 can correspond to an electronic device that is worn or held by a user. The electronic device can include a mobile phone, a smartwatch, smart glasses, or other types of electronic devices. The electronic device 102 includes the sensor module 103 having an inertial sensor 104. The inertial sensor 104 generates sensor data 110 indicative of motion of the electronic device 102, which, can in turn indicate motion of the user.

While the present application may primarily describe embodiments in which the electronic device 102 is a device held or used by the user, principles of the present disclosure extend to other types of electronic devices. For example, the electronic device 102 can be a machine that performs various activities in an automated manner or in other ways. The inertial sensor 104 can generate sensor data 110 indicative of or activity of the machine.

The sensor module 103 may correspond to a module that includes the inertial sensor 104 and circuitry that generates and processes sensor data 110 based on sensor signals generated by the inertial sensor 104. In the simplified example of FIG. 1, the sensor module 103 includes an inertial sensor 104, a control circuit 106, and a classifier 108. In practice, the sensor module 103 may include other components and combinations of components.

In one embodiment, the sensor module 103 corresponds to a single integrated circuit package. In one example, the sensor module includes MEMS sensor corresponding to the inertial sensor 104. The sensor module 103 may also include an application specific integrated circuit (ASIC). The ASIC may include both the control circuit 106 and the classifier 108.

In one embodiment, sensor module 103 includes multiple integrated circuit dies. For example, a first integrated circuit die may include the inertial sensor 104. A second integrated circuit die may include the ASIC that includes the control circuit 106 and the classifier 108. In one embodiment, the sensor module 103 may include a single integrated circuit die that includes the inertial sensor 104, the control circuit 106, and the classifier 108. When the sensor module 103 includes multiple integrated circuit dies, the sensor module 103 may be implemented in a single encapsulated package or in multiple separate encapsulated packages.

FIG. 1 illustrates the classifier 108 as being separate from the control circuit 106. However, in one embodiment, the classifier 108 is part of the control circuit 106. In one embodiment, the control circuit 106, or portions of the control circuit 106, may be implemented separate from the sensor module 103. For example, the electronic device 102 may include one or more processors external to the sensor module 103 that may perform some or all of functions of the control circuit 106.

The sensor module 103 can be implemented in three separate portions. A first portion is a mechanical portion that includes the inertial sensor 104. The inertial sensor 104 may include one or more suspended masses that physically moved based on inertial forces exerted on the electronic device 102. The movement of these one or more masses may be sensed capacitively or in other manners. Accordingly, the inertial sensor 104 may generate capacitive signals corresponding to sensor signals.

A second portion of the sensor module 103 is an analog portion. The analog portion may receive the capacitive sensor signals and converted to voltage-based sensor signals. These voltage-based sensor signals are analog sensor signals. The analog portion may include, among other circuitry, an analog-to-digital converter (ADC) that generates digital sensor signals.

A third portion of the sensor module 103 is a digital portion. The digital portion may receive the digital sensor signals from the analog portion. The digital portion may process the digital sensor signals to generate the inertial sensor data 110. The inertial sensor data 110 represents the inertial forces exerted on the inertial sensor 104. Although the inertial sensor data 110 is shown as being part of the inertial sensor 104, in practice, the control circuit 106 may include the digital portions of the sensor module 103 that generate the inertial sensor data from the inertial sensor signals provided by the inertial sensor 104.

The inertial sensor 104 may include an accelerometer, a gyroscope, or other types of inertial sensors. The inertial sensor 104 may include both a gyroscope and an accelerometer. The accelerometer can include one axis, two axes, or three axes. The gyroscope can also include one axis, two axes, or three axes.

The classifier 108 corresponds to an analysis model trained with a machine learning process to classify the inertial sensor data 110 as corresponding to a particular activity. In the example of an electronic device 102 worn or carried by the user, the classifier 108 may be trained to recognize when the user is walking, running, sitting, standing, climbing stairs, riding a bicycle, performing a bench press exercise, performing an arm curl exercise, performing squat exercises, playing a particular sport, or other types of activities. The classifier 108 may generate classification data 114 indicating the various activities represented in various segments of the sensor data 110.

As set forth above, the classifier 108 is trained with a machine learning process. In one embodiment, the machine learning process utilizes a training set as part of a supervised machine learning process. The training set can include a large number of distinct segments of inertial sensor data each representing a particular activity. Each segment may be labeled with the activity represented by that segment of inertial sensor data. During the training process, the classifier 108 is iteratively trained until the classifier 108 can accurately classify each segment of the inertial sensor data in a way that matches the label of the sensor data. When the training process is complete, the classifier 108 can be utilized to classify activities in real time.

However, there are various difficulties associated with generating a training set. In particular, it can be difficult to determine when one activity stops and another begins. The inertial sensor data typically corresponds to a stream of sensor data over a time interval. During that time interval, multiple different activities may be performed. To generate a training set, it is beneficial to know exactly when one activity stops and another begins. However, this can be computationally very expensive.

The control circuit 106, in accordance with principles of the present disclosure, implements an efficient and effective method for segmenting a stream of inertial sensor data into distinct segments that each represent performance of a particular activity. Each segment ends when a next activity begins. Accordingly, the control circuit 106 generates activity segmentation data 112. The activity segmentation data 112 identifies the distinct segments of a stream of inertial sensor data 110.

In one embodiment, the control circuit 106 performs wavelet transforms on the inertial sensor data 110. The wavelet transforms generate, for the sensor data from a selected window of time, a plurality of wavelet sub-band. Each wavelet sub-band corresponds to a range of frequencies and indicates the energy associated with that range of frequencies in the inertial sensor data. More particularly, in the first top window, we compute the wavelet transform for each channel and select the sub-band yielding the largest energy. The control circuit 106 identifies the highest energy wavelet sub-band in the window of sensor data. The control circuit 106 operates on the principle that the highest energy wavelet sub-band will be different for one activity than for another. Accordingly, if the activity changes from the first half window to the second half window, then it is unlikely that the highest energy sub-band from the first half window will be the highest energy sub-band and the second half window.

After identifying the highest energy sub-band in the first top window, the control circuit 106 generates augmented sensor data. The augmented sensor data includes the original inertial sensor data 110 of the window with the identified highest energy wavelet sub-band from the first top window added back into the inertial sensor data 110.

The control circuit 106 discrepancy between the first half window and the second half window. Details regarding calculation of the discrepancy are provided further below. The discrepancy value is calculated for each window as the window slides across the stream of sensor data. The discrepancy value of each window generates a discrepancy curve as the window slides.

The control circuit 106 determines that there is a change in activity when there is a peak in the discrepancy curve. In one embodiment, the control circuit 106 only determines that there is a change in the activity if the peak in the discrepancy curve is higher than a selected threshold. As each discrepancy value corresponds to the discrepancy between the first half window and the second half window at a particular point in time, the peak of the discrepancy curve corresponds to the point at which the first half window of augmented sensor data is most different than the second half window. This is the point in time at which the activity is changed from the first activity to the second activity.

Calculation of the wavelet and the discrepancy is computationally inexpensive. Accordingly, the identification of transition points between activities in the inertial sensor data 110 is computationally inexpensive and rapid. Furthermore, usage of the discrepancy peak is highly accurate as an indicator of transitions in activity.

Using the wavelet transforms and discrepancy curve as set forth above, the control circuit 106 is able to generate activity segmentation data 112 that indicates the transition points in the inertial sensor data 110 for a selected period of time. With the generation of the activity segmentation data in this manner, labels can quickly be applied to the various segments of the inertial sensor data. Accordingly, the control circuit 106 can assist in generating training set data for training the classifier 108.

In one embodiment, the system 100 includes a remote system 105 communicatively coupled to the electronic device 102 by a network 101. The network 101 can include one or more of a cellular communication network, a Wi-Fi network, a local area network, the Internet, or other types of networks. The electronic device 102 can pass data to the remote system 105 via the network 101. The remote system 105 can pass data to the electronic device via the network 101.

In one embodiment, the remote system 105 is a cloud-based system that assists in one or both of generating training set data and training the classifier 108. The remote system 105 includes processing resources 116, memory resources 118, and communication resources 120. The processing resources 116 can include one or more processors that can process data, execute software instructions, or perform other functions. The memory resources 118 can include one or more memories configured to store data. The data can include inertial sensor data 110, activity segmentation data 112, software instructions for operating the remote system 105, training set data, or other types of data.

The communication resources 120 can include resources for sending and receiving information. The communication resources 120 can include one or more wireless transceivers, wired communication ports, and other types of communication resources for sending and receiving data.

In one embodiment, the remote system receives inertial sensor data 110 from the electronic device 102. The remote system 105 can generate activity segmentation data 122 by performing the wavelet transform, generating augmented sensor data, and generating a discrepancy curve. In other words, in one embodiment, the remote system 105 performs some of the functions ascribed to the control circuit 106 previously.

In one embodiment, the remote system 105 generates training set data based on the activity segmentation data 112/122. The remote system 105 can apply labels to the various segments of inertial sensor data in order to generate labeled training set data. The remote system 105 can then perform a machine learning process that generates classification data 124. The classification data 124 can correspond to a new classifier. The remote system 105 can then push the new classifier data to the electronic device 102. The electronic device 102 then updates the classifier 108 with the new classifier data resulting from the machine learning process. Alternatively, some or all of the machine learning process can be performed by the electronic device 102.

Figure 2:
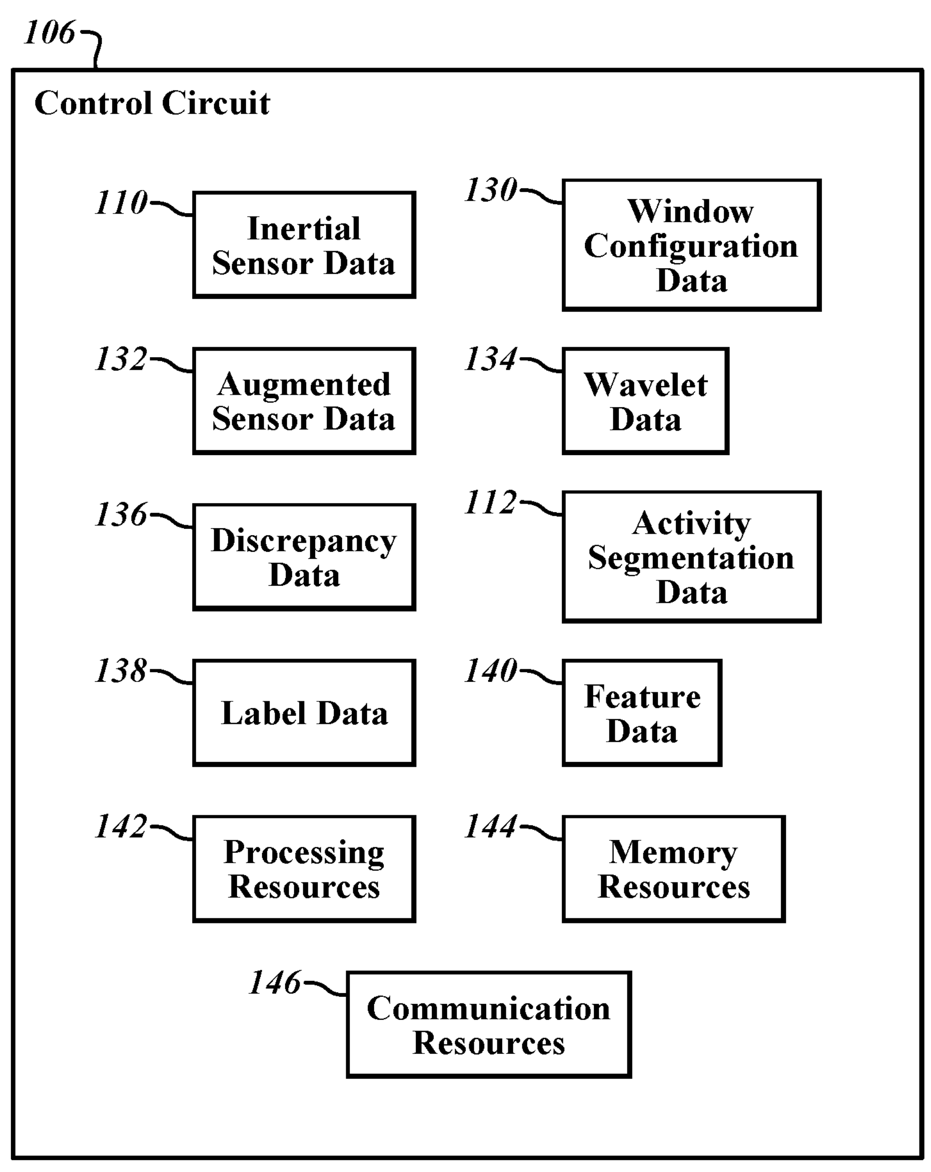
FIG. 2 is a block diagram of a control circuit of a sensor module, in accordance with one embodiment.

FIG. 2 is a block diagram of the control circuit 106 of FIG. 1, in accordance with one embodiment. The control circuit 106 can include processing resources 142, memory resources 144, and communication resources 146. The processing resources 142 can include one or more processors that can process data, execute software instructions, or perform other functions. The memory resources 144 can include one or more memories configured to store data. The data can include inertial sensor data 110, activity segmentation data 112, software instructions for operating the sensor module 103, training set data, or other types of data. The communication resources 146 can include resources for sending and receiving information. The communication resources 146 can include one or more wireless transceivers, wired communication ports, and other types of communication resources for sending and receiving data.

The control circuit 106 stores inertial sensor data 110. As described previously, the inertial sensor data 110 may correspond to a stream of inertial sensor signals provided by the inertial sensor 104 during a selected period of time.

The control circuit 106 stores window configuration data 130. As described previously, the control circuit 106 utilizes a sliding window process to generate activity segmentation data 112. The window corresponds to a selected duration of time. The window is divided into a first half window and a second half window. The window configuration data 130 stores the length of the window and other parameters associated with the window.

The control circuit 106 stores augmented sensor data 132. As set forth previously, the augmented sensor data for a particular window corresponds to the sum of the inertial sensor data 110 for that window and the wavelet sub and that has the highest energy in the first half window.

The control circuit 106 stores label data 134. The wavelet data corresponds to the various sub- and data generated in the wavelet transform. As described previously, the wavelet transform performed on the window of inertial sensor data 110 results in a plurality of wavelet sub-bands each corresponding to a range of frequencies. The label data 134 also stores the energy associated with each wavelet sub-band. The wavelet sub and with the highest energy is selected for generating the augmented sensor data 132.

The control circuit 106 includes the discrepancy data 136. As set forth previously, the control circuit 106 generates a discrepancy curve including a discrepancy value for each window as the window slides across the inertial sensor data 110. A peak in the discrepancy data 136 corresponds to the transition point between one activity and another in the inertial sensor data 110.

The control circuit 106 stores the activity segmentation data 112. The activity segmentation data 112 indicates the segments or transition points between the various activities in the inertial sensor data 110.

In one embodiment, the control circuit 106 stores label data 138. The label data 138 can correspond to labels for each segment of the inertial sensor data 110. As described previously, labels can be provided by the user 138, by the remote system 105, or in some other way.

In one embodiment, the control circuit 106 stores feature data 140. More particularly, the control circuit 106 may generate feature data for the inertial sensor data 110. The features can include the mean, the variance, the energy, the peak, the zero crossing, or other features of the inertial sensor data 110. A training set may include, for each segment, the various features. Furthermore, when the classifier 108 is operating in real time, the control circuit 106 generates the feature data and the classifier 108 classifies a current activity based on the features.

Some of the processes, functions, data, and components described in relation to the control circuit 106 in FIG. 2 can be incorporated in the remote system 105, in one embodiment. Accordingly, the remote system 105 may calculate, utilize, or store the various types of data shown in relation to FIG. 2.

Figure 3:
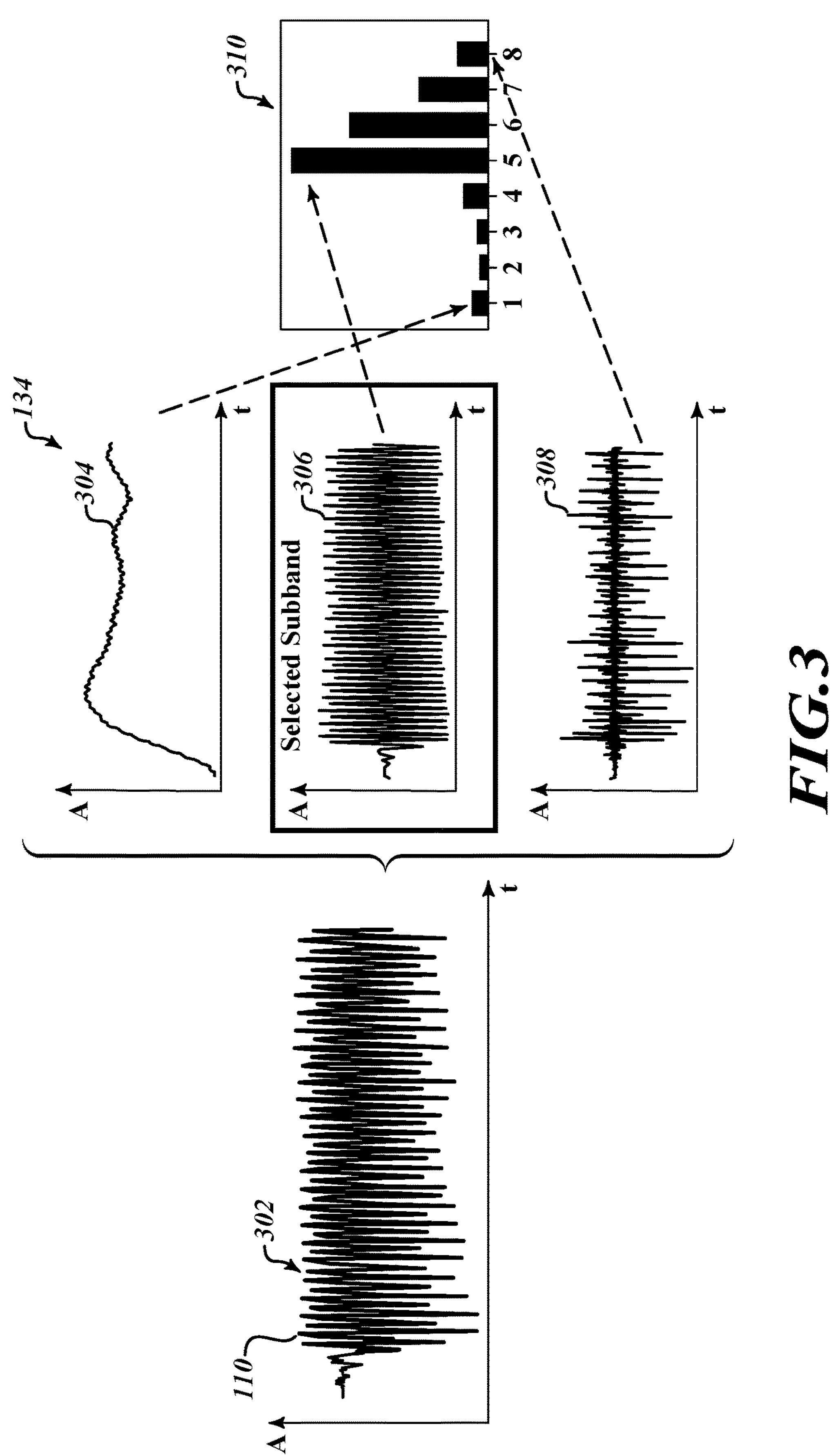
FIG. 3 includes graphs illustrating inertial sensor data, wavelet sub-bands generated from the inertial sensor data, in accordance with one embodiment.

FIG. 3 includes graphs illustrating inertial sensor data, wavelet sub-bands generated from the inertial sensor data, in accordance with one embodiment. The graph 302 corresponds to inertial sensor data 110. The x-axis is time and the y-axis is amplitude. The graphs 304, 306, and 308 correspond to wavelet data 134. The graph 310 illustrates the energy included in each of eight wavelet sub-bands. Each of the eight wavelet sub-bands corresponds to a group or range of frequencies.

The graph 304 corresponds to a first wavelet sub-band generated by performing a wavelet transform on the inertial sensor data 110. As can be seen in the graph 310, the first wavelet sub-band is relatively low energy. The graph 306 corresponds to the fifth wavelet sub-band. As can be seen in the graph 310, the fifth wavelet sub-band has the highest energy of all of the sub-bands. Accordingly, the fifth sub-band would be selected for generating the augmented sensor data for this particular segment of inertial sensor data. The graph 308 corresponds to wavelet sub-bands number eight. As can be seen in the graph 310, the wavelet sub and the break is relatively low energy. For simplicity, the graphs of only three of the wavelet sub-bands are shown in FIG. 3.

Figure 4A:
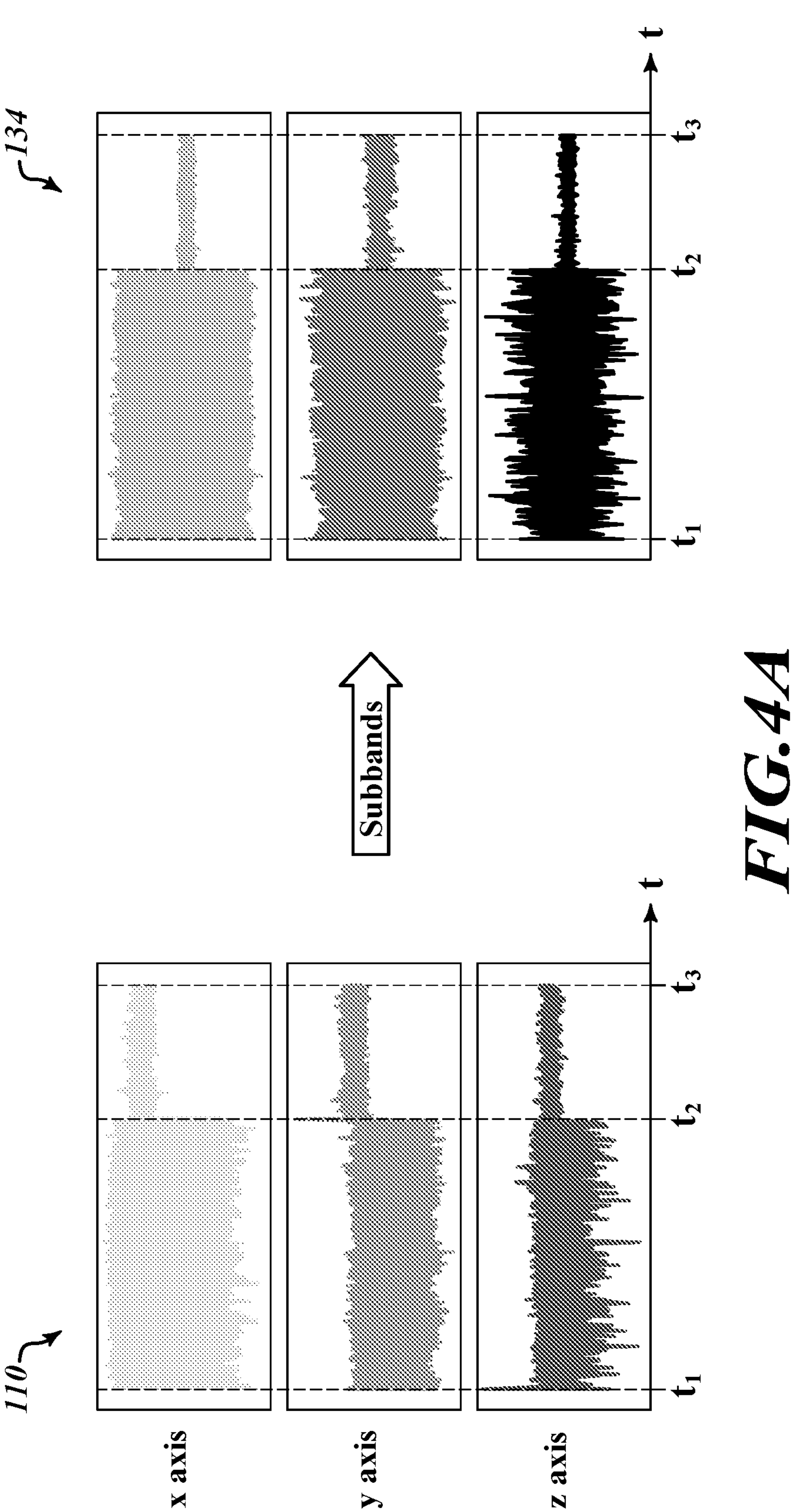
FIG. 4A illustrates graphs of sensor data and augmented sensor data for a plurality of axes of the inertial sensor, in accordance with one embodiment.

FIG. 4A illustrates graphs of sensor data and augmented sensor data for a plurality of axes of the inertial sensor, in accordance with one embodiment. In particular, the left side of the graph includes inertial sensor data 110 representing a range of time between times t1 and t3 for each of three inertial sensor axes. At time t2, there is a transition between activities.

The right side of the graph of FIG. 4A corresponds to wavelet data 134. More particularly, the graph of FIG. 4A illustrates the highest energy sub-band for each of the three axes. As set forth previously, the highest energy sub-band is selected based on the energy of the first window. In each of the three axes, after the transition, the selected wavelet sub-band has relatively low energy. This is based on the principle that the highest energy sub-bands for one activity will be different than the highest energy wavelet sub-bands for another activity.

Figure 4B:
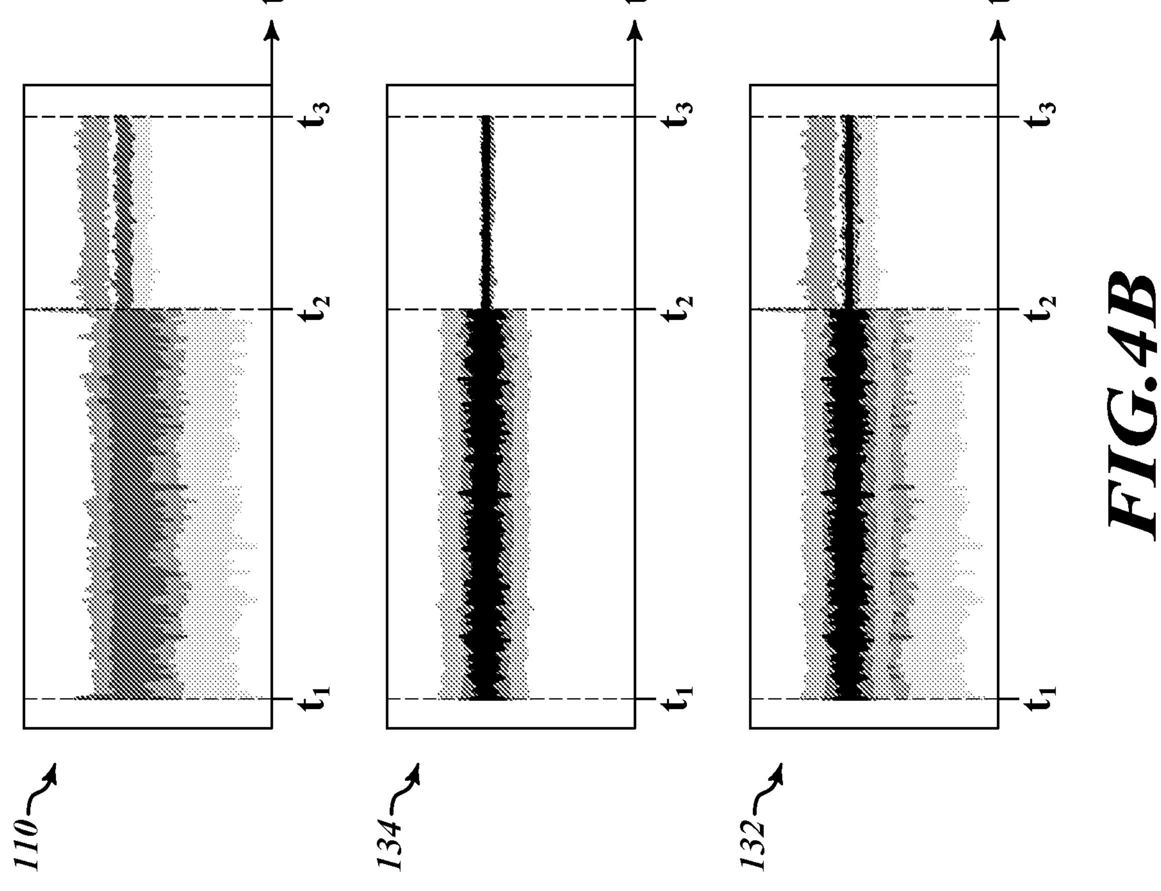
FIG. 4B includes graphs illustrating inertial sensor data, wavelet sub-bands, and augmented sensor data, in accordance with one embodiment.

FIG. 4B includes graphs illustrating inertial sensor data, wavelet sub-bands, and augmented sensor data, in accordance with one embodiment. More particularly, the inertial sensor data 110 in FIG. 4B is the combination of all three axes of inertial sensor data. The wavelet data 134 includes the selected wavelet sub-band for each of the three axes. The augmented sensor data 132 illustrates the sum of this reaction of inertial sensor data and the selected wavelet sub-band data from each of the axes. As will be set forth in more detail below, this augmented sensor data is useful in identifying the transition points in the inertial sensor data.

Figure 5A:
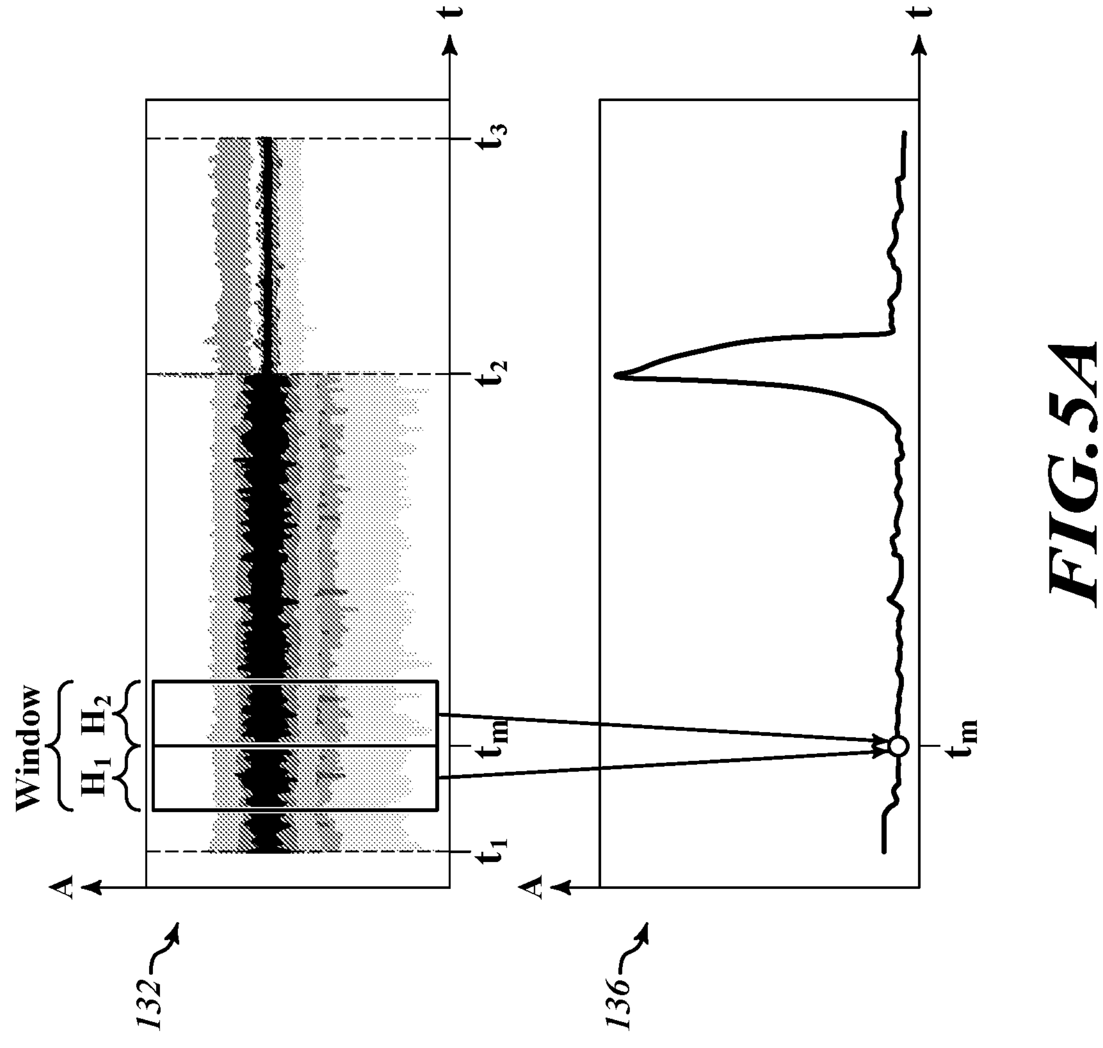
FIG. 5A includes graphs illustrating augmented sensor data and discrepancy values, in accordance with one embodiment.

FIG. 5A includes graphs illustrating augmented sensor data and discrepancy values, in accordance with one embodiment. The upper graph in FIG. 5A illustrates the augmented sensor data 132 from FIG. 4B. The lower graph in FIG. 5A illustrates the discrepancy curve 136.

The upper graph illustrates the window the slides across the augmented sensor data. The window is divided into a first-half window H1 and the second half window H2. The time tm corresponds to the midpoint of the window. The time tm slides across the augmented sensor data 132.

The discrepancy data 136 includes a discrepancy value for each window. More particularly, the discrepancy value corresponds to the discrepancy calculation at the time tm. As the window slides across the augmented sensor data 132, tm also slides across any discrepancy value is calculated for each window.

In one embodiment, the discrepancy values calculated based on covariance matrices of the first half window, the second half window, and the total window. The window includes a plurality of samples of the augmented sensor data 132. Each Window has half of the samples. The covariance matrix is calculated for the samples in each window or half window. The covariance matrix of samples in the first half window H1 is represented by the symbol $\Sigma_1$. The covariance matrix of samples in the first half window H2 is represented by the symbol $\Sigma_2$. The covariance matrix of samples of the entire window is represented by the symbol $\Sigma_{tot}$. The control circuit 106 calculates the determinant of each of the covariance matrices ($\det\Sigma_1$, $\det\Sigma_2$, $\det\Sigma_{tot}$). Finally, the discrepancy value D for a window of augmented sensor data is calculated in the following manner:

$$D = \det\sum_{tot} \Big/ \left(\left(\det\sum_1\right)^{1/2}\left(\det\sum_2\right)^{1/2}\right).$$

Although a particular example of a discrepancy calculation has been described, other methods of calculating a discrepancy can be utilized without departing from the scope of the present disclosure.

Figure 5B:
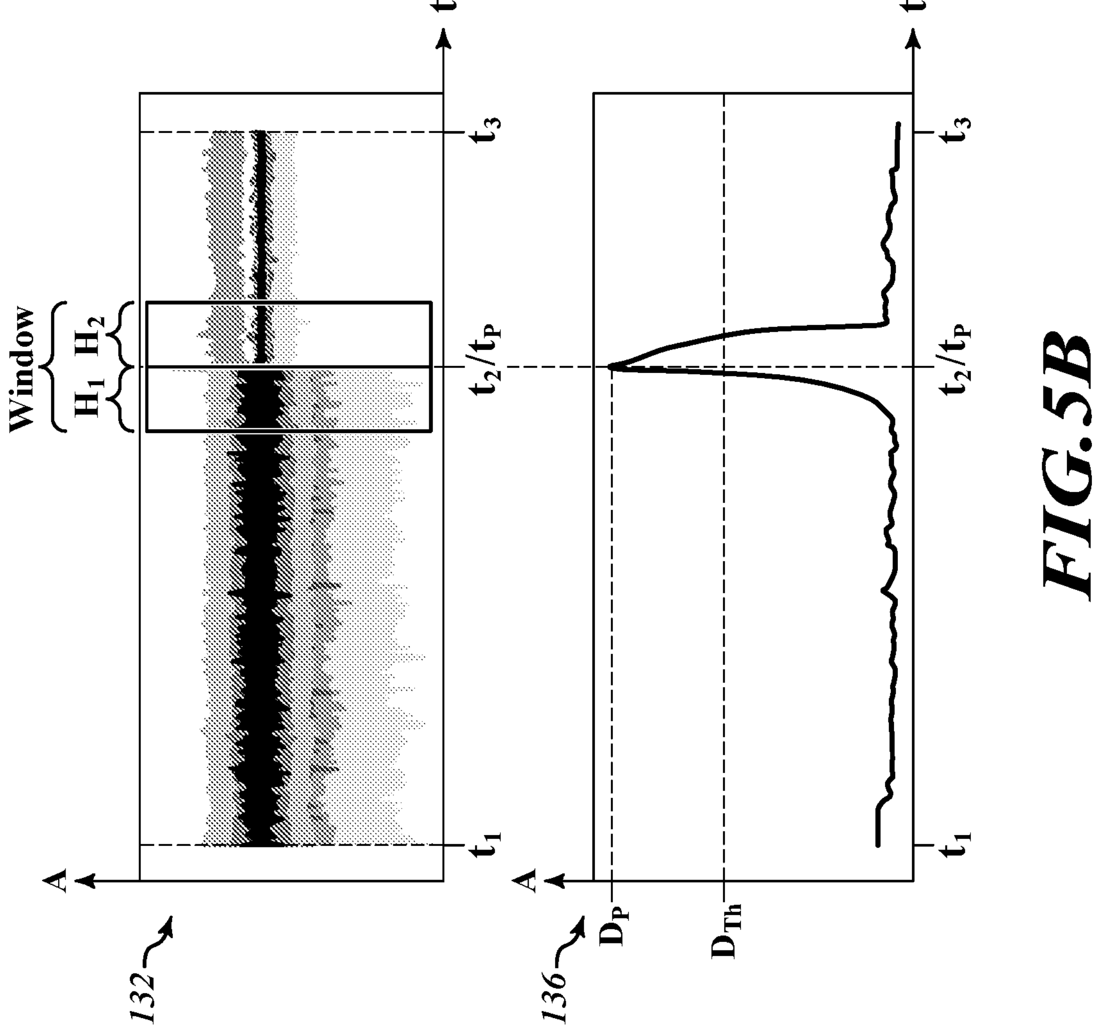
FIG. 5B includes graphs illustrating augmented sensor data and discrepancy values, in accordance with one embodiment.

FIG. 5B illustrates the augmented sensor data 132 and the discrepancy data 136 from FIG. 5A, but with the window having slid all the way to the point that the midpoint tm of the window is at time t2. The discrepancy data 136 shows that there is a peak discrepancy Dp in the discrepancy curve at time t2. FIG. 5B also illustrates a threshold discrepancy Dth. In one embodiment, a discrepancy people only be used to identify a transition point if the value of the discrepancy peak is greater than a threshold discrepancy. The control circuit 106 can utilize a peak detection algorithm to identify the peak. As set forth previously, the peak corresponds to a transition between two activities.

Figures 6A, 6B, 6C:
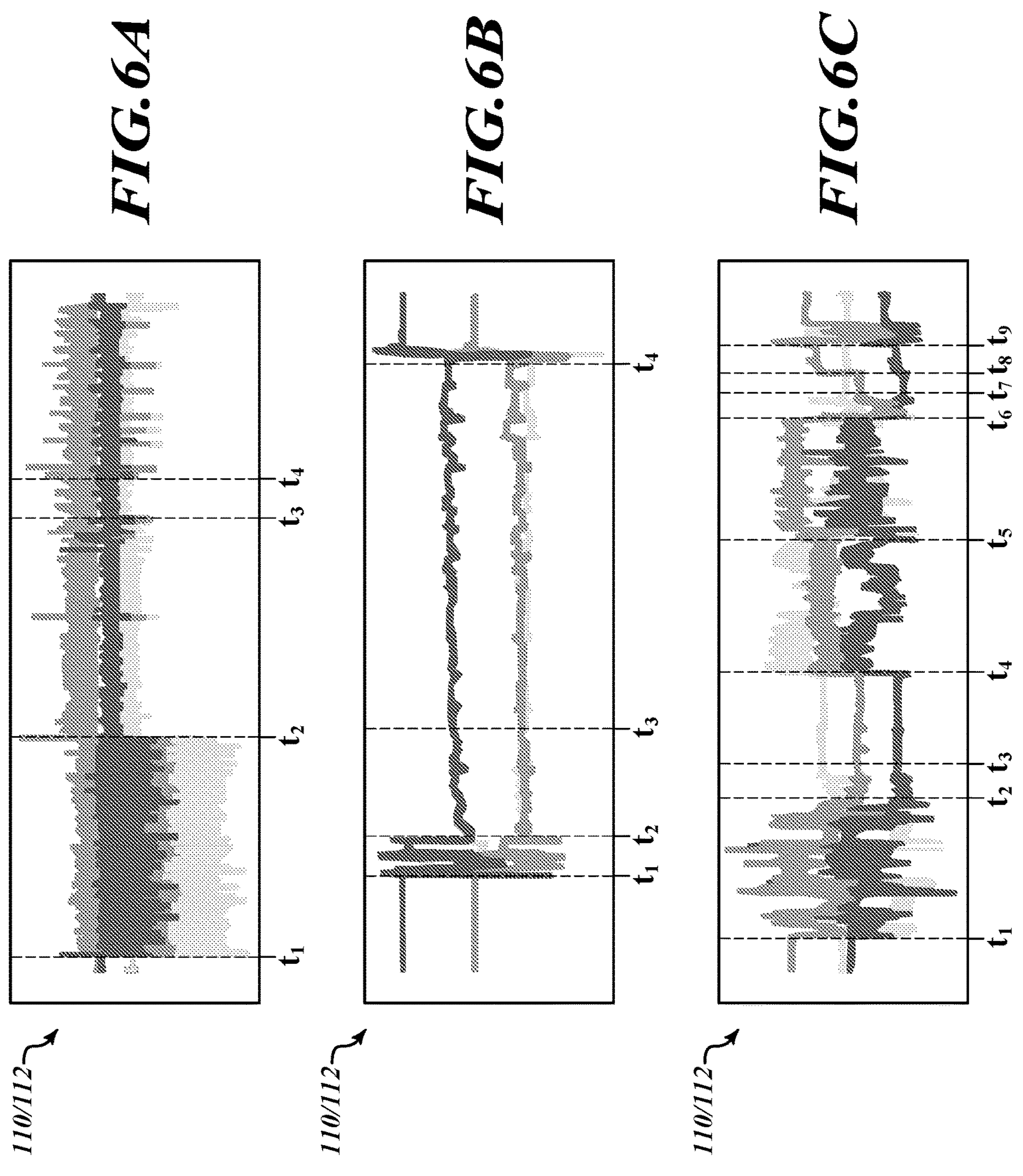
FIGS. 6A-6C includes graphs illustrating augmented sensor data that has been segmented, in accordance with one embodiment.

FIGS. 6A-6C includes graphs illustrating augmented sensor data that has been segmented, in accordance with one embodiment. The graph of FIG. 6A illustrates a stream of sensor data 110 annotated with activity segmentation data 112. The activity segmentation data 112 identifies a first activity between times t1 and t2. At time t2, there is a transition in activity. A second activity is shown between times t2 and t3. A third activity is shown between times t3 and t4. A fourth activity begins at time t4.

The graph of FIG. 6B illustrates a stream of sensor data 110 annotated with activity segmentation data 112. The activity segmentation data 112 identifies a first activity between times t1 and t2. At time t2, there is a transition in activity. A second activity is shown between times t2 and t3. A third activity is shown between times t3 and t4. A fourth activity begins at time t4.

The graph of FIG. 6C illustrates a stream of sensor data 110 annotated with activity segmentation data 112. The activity segmentation data 112 identifies a first activity between times t1 and t2. At time t2, there is a transition in activity. A second activity is shown between times t2 and t3. A third activity is shown between times t3 and t4. A fourth activity begins at time t4. A fifth activity begins at time t5. A sixth activity begins at time t6. A seventh activity begins at time t7. An eighth activity begins at time t8. A ninth activity begins at time t9.

With reference to the graph of FIG. 6A, automatic segmentation simplifies data classification by propagating the label over the entire detecting segment. In one example, a user provides an input to the electronic device providing a label for an activity has begun at time t1. The control circuit 106, the remote system 105, can propagate this label all the way until time t2, when a next activity is detected. The control circuit 106 may cause the electronic device 102 to prompt the user to provide a new label when a new activity is detected. This new label can then be propagated until the next transition is detected. In this way training set data can be collected for a machine learning process.

Figure 7A:
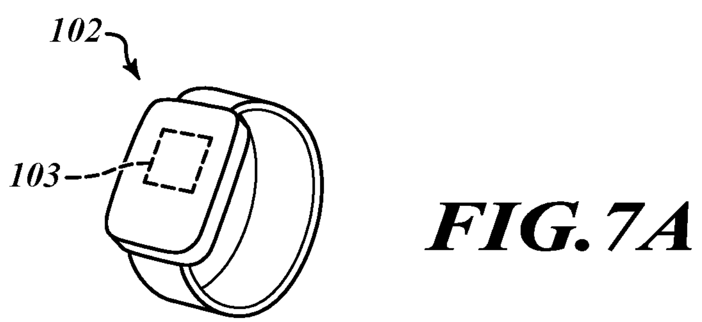
FIGS. 7A-7C are illustrations of electronic devices that include inertial sensors, in accordance with one embodiment.
Figure 7B:
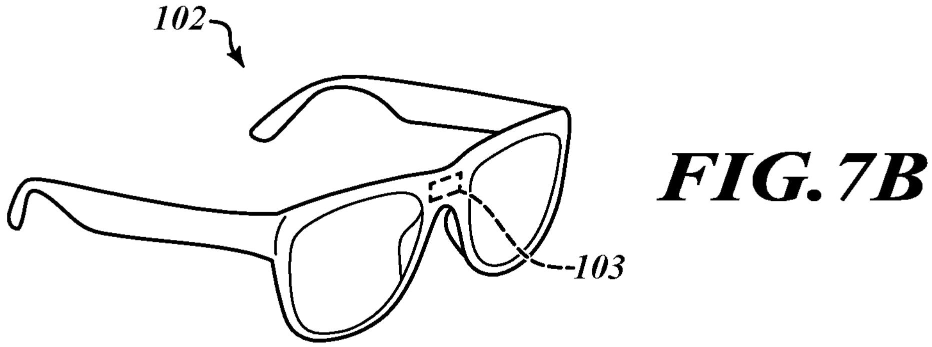
Figure 7C:
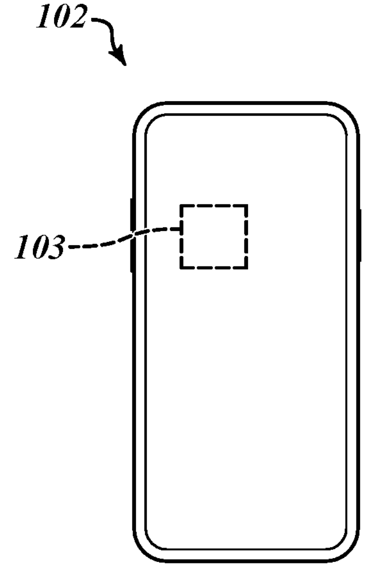

FIGS. 7A-7C are illustrations of electronic devices that include inertial sensors, in accordance with one embodiment. In FIG. 7A, the electronic device 102 is a smart watch with a sensor module 103 embedded therein. The smartwatch can include a display by which the user can enter labels and by which prompts can be provided to the user. In FIG. 7B, the electronic device 102 is smart glasses including a sensor module 103 embedded therein. The smart glasses can include a display that can prompt the user to provide a label. The smart glasses can include one or more input areas by which a user can input a label. In FIG. 7C, the electronic device 102 is a smart phone. The smart phone can include a display by which the user can enter labels and by which prompts can be provided to the user.

Figure 8:
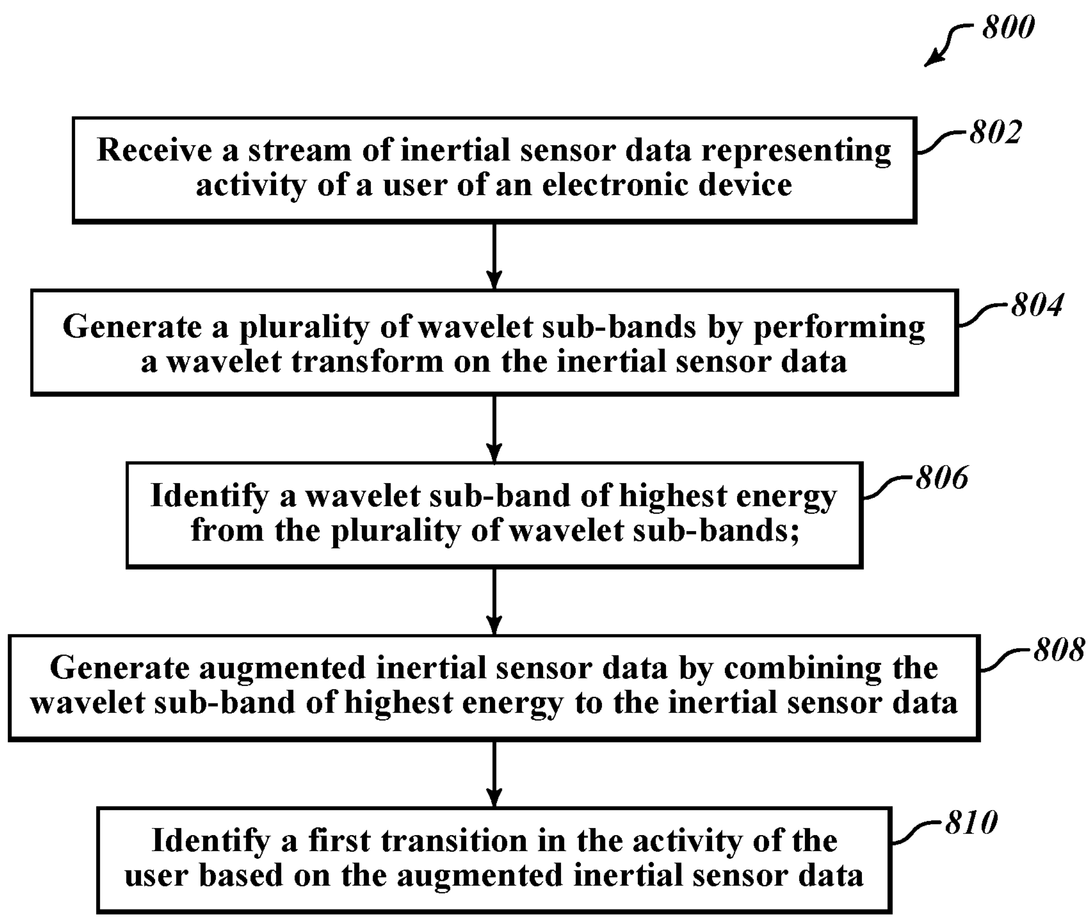
FIG. 8 is a flow diagram of a method for analyzing inertial sensor data, in accordance with one embodiment.

FIG. 8 is a flow diagram of a method 800 for analyzing inertial sensor data, in accordance with one embodiment. The method 800 can utilize systems, components, and processes described in relation to FIGS. 1-7C. At 802, the method 800 includes receiving a stream of inertial sensor data representing activity of a user of an electronic device. At 804, the method 800 includes generating a plurality of wavelet sub-bands by performing a wavelet transform on the inertial sensor data. At 806, the method 800 includes identifying a wavelet sub-band of highest energy from the plurality of wavelet sub-bands. At 808, the method 800 includes generating augmented inertial sensor data by combining the wavelet sub-band of highest energy to the inertial sensor data. At 810, the method 800 include identifying a first transition in the activity of the user based on the augmented inertial sensor data.

Figure 9:
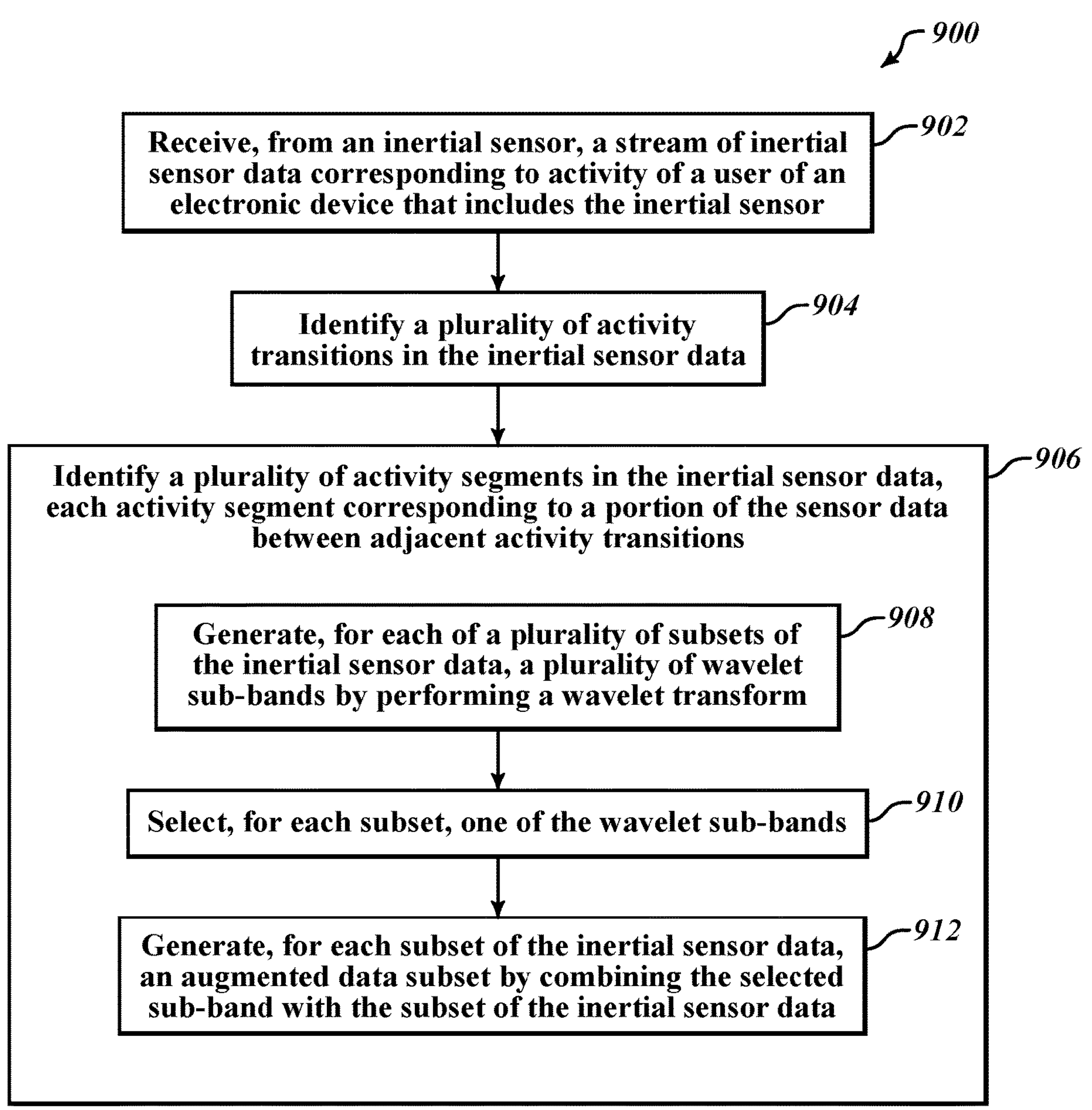
FIG. 9 is a flow diagram of a method for analyzing inertial sensor data, in accordance with one embodiment.

FIG. 9 is a flow diagram of a method for analyzing inertial sensor data, in accordance with one embodiment. The method 900 can utilize systems, components, and processes described in relation to FIGS. 1-7C. At 902, the method 900 includes receiving, from an inertial sensor, a stream of inertial sensor data corresponding to activity of a user of an electronic device that includes the inertial sensor. At 904, the method 900 includes identifying a plurality of activity transitions in the inertial sensor data. At 906, the method 900 includes identifying a plurality of activity segments in the inertial sensor data, each activity segment corresponding to a portion of the sensor data between adjacent activity transitions. At 908, identifying the activity transitions includes generating, for each of a plurality of subsets of the inertial sensor data, a plurality of wavelet sub-bands by performing a wavelet transform. At 908, identifying the activity transitions includes selecting, for each subset, one of the wavelet sub-bands. At 910, identifying the activity transitions includes generating, for each subset of the inertial sensor data, an augmented data subset by combining the selected sub-band with the subset of the inertial sensor data.

In one embodiment, a method includes receiving a stream of inertial sensor data representing activity of a user of an electronic device, generating a plurality of wavelet sub-bands by performing a wavelet transform on the inertial sensor data, and identifying a wavelet sub-band of highest energy from the plurality of wavelet sub-bands. The method includes generating augmented inertial sensor data by combining the wavelet sub-band of highest energy to the inertial sensor data and identifying a first transition in the activity of the user based on the augmented inertial sensor data.

In one embodiment, a method includes receiving, from an inertial sensor, a stream of inertial sensor data corresponding to activity of a user of an electronic device that includes the inertial sensor, identifying a plurality of activity transitions in the inertial sensor data, and identifying a plurality of activity segments in the inertial sensor data, each activity segment corresponding to a portion of the sensor data between adjacent activity transitions. Identifying the activity transitions includes generating, for each of a plurality of subsets of the inertial sensor data, a plurality of wavelet sub-bands by performing a wavelet transform, selecting, for each subset, one of the wavelet sub-bands, and generating, for each subset of the inertial sensor data, an augmented data subset by combining the selected sub-band with the subset of the inertial sensor data.

In one embodiment, an electronic device, includes an inertial sensor configured to generate a stream of inertial sensor data based on activity of a user and a control circuit coupled to the inertial sensor. The control circuit is configured to receive the stream, generate a plurality of wavelet sub-bands by performing a wavelet transform on the inertial sensor data and identify a wavelet sub-band of highest energy from the plurality of wavelet sub-bands. The control circuit is configured to generate augmented inertial sensor data by combining the wavelet sub-band of highest energy to the inertial sensor data and identify a transition in the activity of the user based on the augmented inertial sensor data.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:

receiving a stream of inertial sensor data representing activity of a user of an electronic device;

generating a plurality of wavelet sub-bands by performing a wavelet transform on the inertial sensor data;

identifying a wavelet sub-band of highest energy from the plurality of wavelet sub-bands;

generating augmented inertial sensor data by combining the wavelet sub-band of highest energy to the inertial sensor data; and identifying a first transition in the activity of the user based on the augmented inertial sensor data.

2. The method of claim 1, comprising performing a sliding window process on the stream of sensor data, the sliding window process including:

generating, from the stream of inertial sensor data, a first sequence of windows each including a number of samples of the inertial sensor data and offset from each other in time by at least one sample of the inertial sensor data;

generating, from each window, a first half window including a first half of the number of samples; and generating, from each window, a second half window including a second half of the number of samples.

3. The method of claim 2, wherein identifying the first transition includes calculating a discrepancy curve for the sequence of windows.

4. The method of claim 3, wherein the discrepancy curve includes, for each window, a discrepancy value between the first half window and the second half window.

5. The method of claim 4, wherein identifying the first transition includes:

identifying a peak in the discrepancy curve;

comparing the peak to a threshold discrepancy value; and if the peak is greater than the threshold discrepancy value identifying the first transition as a time corresponding to the discrepancy peak.

6. The method of claim 5, comprising:

generating, from the stream of inertial sensor data, a second sequence of windows for a period of time after the first sequence of windows; and identifying a second transition in the activity of the user in the second sequence of windows.

7. The method of claim 6, comprising identifying an activity segment of the user as corresponding to a set of samples of the inertial sensor data between the first activity transition and the second activity transition.

8. The method of claim 4, wherein calculating the discrepancy value for a window includes:

calculating a first covariance matrix for the first half window;

calculating a second covariance matrix for the second half window;

calculating a third covariance matrix from the window; and calculating the logarithm of the ratio between a determinant of the third covariance matrix and a product of a determinant of the first covariance matrix and a determinant of the second covariance matrix.

9. A method, comprising:

receiving, from an inertial sensor, a stream of inertial sensor data corresponding to activity of a user of an electronic device that includes the inertial sensor;

identifying a plurality of activity transitions in the inertial sensor data; and identifying a plurality of activity segments in the inertial sensor data, each activity segment corresponding to a portion of the sensor data between adjacent activity transitions, wherein identifying the activity transitions includes:

generating, for each of a plurality of subsets of the inertial sensor data, a plurality of wavelet sub-bands by performing a wavelet transform;

selecting, for each subset, one of the wavelet sub-bands; and generating, for each subset of the inertial sensor data, an augmented data subset by combining the selected sub-band with the subset of the inertial sensor data.

10. The method of claim 9, comprising training a classifier model of the electronic device to classify activities with a machine learning process using the activity segments.

11. The method of claim 10, wherein training the classifier model includes generating a labeled training set by labeling each of the activity segments and using the labeled training set in the machine learning process.

12. The method of claim 11, wherein labeling each of the activity segments includes:

identifying a first activity transition;

applying a label to the sensor data after the first activity transition; and propagating the label until a second activity transition is identified.

13. The method of claim 10, wherein the classifier model is a decision tree model.

14. The method of claim 9, comprising performing, for each subset of the inertial sensor data, a sliding window process including:

generating, from the subset of inertial sensor data, a sequence of windows each including a number of samples of the subset inertial sensor data and offset from each other in time by at least one sample of the inertial sensor data;

generating, from each window, a first half window including a first half of the number of samples; and generating, from each window, a second half window including a second half of the number of samples.

15. The method of claim 14, wherein identifying an activity transition includes, for each subset of the inertial sensor data, calculating a discrepancy curve for the sequence of windows.

16. The method of claim 15, wherein the discrepancy curve includes, for each window, a discrepancy value between the first half window and the second half window.

17. The method of claim 16, wherein identifying the first transition includes:

identifying a peak in the discrepancy curve;

comparing the peak to a threshold discrepancy value; and if the peak is greater than the threshold discrepancy value identifying the first transition as a time corresponding to the discrepancy peak.

18. An electronic device, comprising:

an inertial sensor configured to generate a stream of inertial sensor data based on activity of a user;

a control circuit coupled to the inertial sensor and configured to:

receive the stream;

generate a plurality of wavelet sub-bands by performing a wavelet transform on the inertial sensor data;

identify a wavelet sub-band of highest energy from the plurality of wavelet sub-bands;

generate augmented inertial sensor data by combining the wavelet sub-band of highest energy to the inertial sensor data; and identify a transition in the activity of the user based on the augmented inertial sensor data.

19. The electronic device of claim 18, comprising a classifier model configured to classify the activity of the user, wherein the control circuit is configured to divide the stream of sensor data into activity segments for the classifier model based, in part, on the transition.

20. The electronic device of claim 19, wherein the classifier model is a decision tree model.

* * * * *